United States Patent [19]

Randolph et al.

[11] Patent Number: 5,534,657

[45] Date of Patent: Jul. 9, 1996

[54] ISOPARAFFIN-OLEFIN ALKYLATION

[75] Inventors: Bruce B. Randolph, Bartlesville, Okla.; Ronald G. Abbott, Kingwood, Tex.; Jonathan E. Child, Sewell; Kenneth J. Del Rossi, Woodbury, both of N.J.

[73] Assignee: Phillips Petroleum Company, Bartlesville, Okla.

[21] Appl. No.: 376,176

[22] Filed: Jan. 20, 1995

Related U.S. Application Data

[63] Continuation-in-part of Ser. No. 877,336, May 1, 1992, and a continuation-in-part of Ser. No. 856,270, Mar. 23, 1992, which is a continuation-in-part of Ser. No. 719,879, Jun. 21, 1991, abandoned.

[51] Int. Cl.$^6$ .................................................. C07C 2/62
[52] U.S. Cl. .......................... 585/723; 585/724; 585/730
[58] Field of Search ..................................... 585/723, 724, 585/726, 721, 730

[56] References Cited

U.S. PATENT DOCUMENTS

| | | | |
|---|---|---|---|
| 2,615,908 | 10/1952 | McCaulay et al. | 260/438 |
| 3,531,546 | 9/1970 | Hervert | 260/683.51 |
| 3,567,634 | 3/1971 | Billings et al. | 252/8.55 |
| 3,778,489 | 12/1973 | Parker et al. | 260/683.43 |
| 3,795,712 | 3/1974 | Torck et al. | 260/671 |
| 3,856,764 | 12/1974 | Throckmorton et al. | 260/82.1 |
| 4,025,577 | 5/1977 | Siskin et al. | 260/683.51 |
| 4,094,924 | 6/1978 | Siskin et al. | 260/683.51 |
| 4,207,423 | 6/1980 | Makovec et al. | 585/332 |
| 4,636,488 | 1/1987 | Imai et al. | 502/172 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |

OTHER PUBLICATIONS

*Hydrofluoric Acid Alkylation*, Phillips Petroleum Co. 1946, Ch. 10, "Metallurgy, Corrosion, and Materials of Construction".
H. H. Uhlig, Ed, *Corrosion Handbook*, Wiley, 1948, p. 133.
R. H. Perry and C. H. Chilton, Eds., *Chemical Engineers's Handbook*, 5th Ed., McGraw–Hill, 1973, pp. 23–18.
H. H. Uhlig, Ed, *Corrosion Handbook*, Wiley, 1948, p. 911.
L. F. Albright et al., "Alkylation of Isobutane with $C_4$ Olefins", 27 *Ind. Eng. Chem. Res.*, 381–386 (1988).
*Handbook of Petroleum Refining Processes* 23–28 (R. A. Meyers, ed., 1986).

*Primary Examiner*—Asok Pal
*Attorney, Agent, or Firm*—Charles W. Stewart

[57] ABSTRACT

A novel alkylation catalyst is described which is used in processes for alkylating olefin hydrocarbons with isoparaffin hydrocarbons to produce high octane alkylate products suitable for use as blending components of gasoline motor fuel. The novel catalyst comprises a mixture of a hydrogen halide, a sulfone and water and has suitable corrosion properties which permit its utilization in alkylation process systems. The novel alkylation catalyst is utilized in a novel process for alkylating olefin hydrocarbons with isoparaffin hydrocarbons.

19 Claims, 8 Drawing Sheets

PERFORMANCE OF HF/SULFOLANE MIXTURES

ISOPARAFFIN-OLEFIN ALKYLATION

This is a continuation-in-part of application Ser. No. 07/877,336, filed May 1, 1992, now pending, and a continuation-in-part of application Ser. No. 07/856,270, filed Mar. 23, 1992, now abandoned, which is a continuation-in-part of application Ser. No. 07/719,879, filed Jun. 21, 1991, now abandoned.

The present invention relates to a hydrocarbon conversion process and a catalyst composition to be utilized in said hydrocarbon conversion process. The invention further relates to a method of retardation or inhibition of corrosion in alkylation process systems by use of a novel composition.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and it preferably contains hydrocarbons having seven to nine carbon atoms. In order to have the highest quality gasoline blending stock, it is preferred that the hydrocarbons formed in the alkylation process be highly branched.

One of the more desirable alkylation catalysts is hydrofluoric acid, however, the use of hydrofluoric acid as an alkylation catalyst has certain drawbacks. One of the primary problems with the use of hydrofluoric acid as an alkylation catalyst is that it is a highly corrosive substance, and it is toxic to human beings. The toxicity of hydrofluoric acid to human beings is further complicated by the fact that anhydrous hydrogen fluoride acid is typically a gas at normal atmospheric conditions of one atmosphere of pressure and 70° F. It is possible for the vapor pressure of hydrofluoric acid at standard atmospheric conditions to create certain safety concerns when it is exposed to the atmosphere. These safety concerns are created by the ease with which hydrofluoric acid is vaporized and released into the atmosphere.

In spite of the potential problems with human toxicity and the corrosive characteristics of hydrofluoric acid, industry has in the past determined that the benefits from the use of hydrofluoric acid as an alkylation catalyst outweigh the potential problems. For instance, hydrofluoric acid is an extremely effective alkylation catalyst in that it permits the reaction of olefins by isoparaffins at low process pressures and process temperatures. HF is particularly suited for use as a catalyst in the alkylation of butylenes and, in the case of the alkylation of propylene and amylenes, HF has been used as an effective catalyst whereas other alkylation catalysts, such as sulfuric acid, have been found to be not as effective in such alkylation services. Additionally, the alkylate formed from a hydrofluoric acid alkylation process is of a very high quality having such desirable properties as being a mixture of highly branched hydrocarbon compounds that provide a high octane motor fuel. Generally, it has been found that the alkylate produced by a hydrofluoric acid alkylation process has a higher octane value than that produced by typical sulfuric acid alkylation processes. Thus, it would be desirable to use an alkylation catalyst that has the desirable features of the hydrofluoric acid catalyst but without having its high vapor pressure.

In searching for a suitable composition to replace hydrofluoric acid as an alkylation catalyst having the desirable properties of providing for a high quality alkylate reaction product and a reduced vapor pressure, one problem encountered is that of the corrosive nature of such substitute catalysts. Not only must such a substitute alkylation catalyst have the aforementioned desirable physical properties, it must also be reasonably non-corrosive to the metal components, such as, for example, pressure vessels, piping, equipment and other appurtenances, of an alkylation process system in order for the catalyst to be commercially viable. In the case of the use of hydrogen fluoride as an alkylation catalyst, the art teaches that, to minimize its corrosive effect upon the carbon steel components of this alkylation process system, it is best for the hydrogen fluoride to be used with a minimal concentration of water. In fact, the corrosive effects of aqueous hydrogen fluoride on carbon steel increases with increasing concentrations of water. As for the compositions proposed as being suitable substitutes for hydrogen fluoride as an alkylation catalyst, all have been found to also be highly corrosive to carbon steel.

It is also desirable to provide an additive which decreases the cloud forming tendency of HF without compromising its activity as an isoparaffin:olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,53 1,546 to Hervert discloses a $HF-CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,094,924 to Siskin et al. report the use of alkylation catalyst compositions containing HF, a metal halide, and sulfolane.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

U.S. Pat. No. 5,073,674 to Olah relates to an alkylation process which uses a liquid onium polyhydrogen fluoride complex as reaction medium and catalyst. The Olah patent states that the disclosed complexing method reduces the volatility of the hydrofluoric acid.

Research efforts have been directed to developing additives which not only suppress the cloud forming tendency of strong Bronsted acids (such as HF) but also preserve the activity of the strong acid for isoparaffin:olefin alkylation. While certain of these additives have been found to be useful vapor pressure suppressants, some have been found to be highly corrosive toward carbon steel which is a commonly used material of construction in HF alkylation process units. The problem of catalyst corrosivity is critical because the cost of retrofitting an existing HF alkylation process unit with corrosion-resistant alloy equipment could preclude replacing the concentrated HF catalyst with the safer HF/additive mixture.

It is, therefore, an object of this invention to provide a novel alkylation catalyst having the desirable property of providing a high quality alkylate reaction product when utilized in the alkylation of olefins with paraffins but having a lower vapor pressure than that of hydrofluoric acid.

A further object of this invention is to provide an alkylation catalyst composition having suitable corrosion properties when utilized in an alkylation process system such as one constructed of carbon steel.

A still further object of this invention is to provide a novel alkylation catalyst composition which can be used in an alkylation process system without causing commercially excessive corrosion of the process system's equipment.

A yet further object of this invention is to provide a process for the alkylation of olefins with paraffins in the presence of an alkylation catalyst having the desirable property of having a reduced vapor pressure but which produces a high quality alkylate product.

Another object of this invention is to provide a method for inhibiting corrosion of metal by a corrosive medium.

Yet another object of this invention is to provide a method for inhibiting or retarding the corrosive nature of compositions that can suitably be used in processes and process systems for the alkylation of olefins with paraffins.

Thus, the process of the present invention relates to the alkylation of a hydrocarbon mixture comprising olefins and paraffins with a catalyst composition comprising the components of a hydrogen halide, a sulfone, and water. In accordance with the present invention, it has been found that a mixture of hydrofluoric acid, sulfolane, and water, is an effective isoparaffin: olefin alkylation catalyst, exhibits markedly reduced tendency to form vapor clouds upon release, and is surprisingly less corrosive than an anhydrous mixture of HF and sulfolane.

Another embodiment of the present invention relates to a method of inhibiting corrosion of metal by a corrosive medium comprising a hydrogen halide and a sulfone by incorporating into said corrosive medium water in an amount sufficient to inhibit corrosion.

The invention further provides a process for alkylating an isoparaffin with an olefin in the presence of a catalyst composition comprising a concentration of hydrofluoric acid sufficient to provide commercially useful catalytic alkylation activity, a concentration of sulfolane in solution with said hydrofluoric acid sufficient to maintain the vapor pressure of the solution comprising HF and sulfolane at less than about atmospheric pressure under commercial isoparaffin: olefin alkylation process conditions, and from about 0.25 to about 10 weight percent water.

The invention thus provides a method for decreasing the rate of corrosive attack on carbon steel by a mixture of HF and sulfolane, said method comprising adding a controlled amount of water to said HF and sulfolane mixture such that the resulting HF/sulfolane/water mixture contains from about 0.25 to about 10 weight percent water.

The composition of the present invention comprises the components of a hydrogen halide, a sulfone, and water.

BRIEF DESCRIPTION OF DRAWINGS

Other objects and advantages of the invention will be apparent from the foregoing detailed description of the invention, the appended claims, and the drawings in which:

FIG. 5b is a plot of $C_9+$ byproduct in the alkylate product as a function of weight percent sulfolane in HF under the conditions set forth with reference to FIG. 5a.

Figure 1:
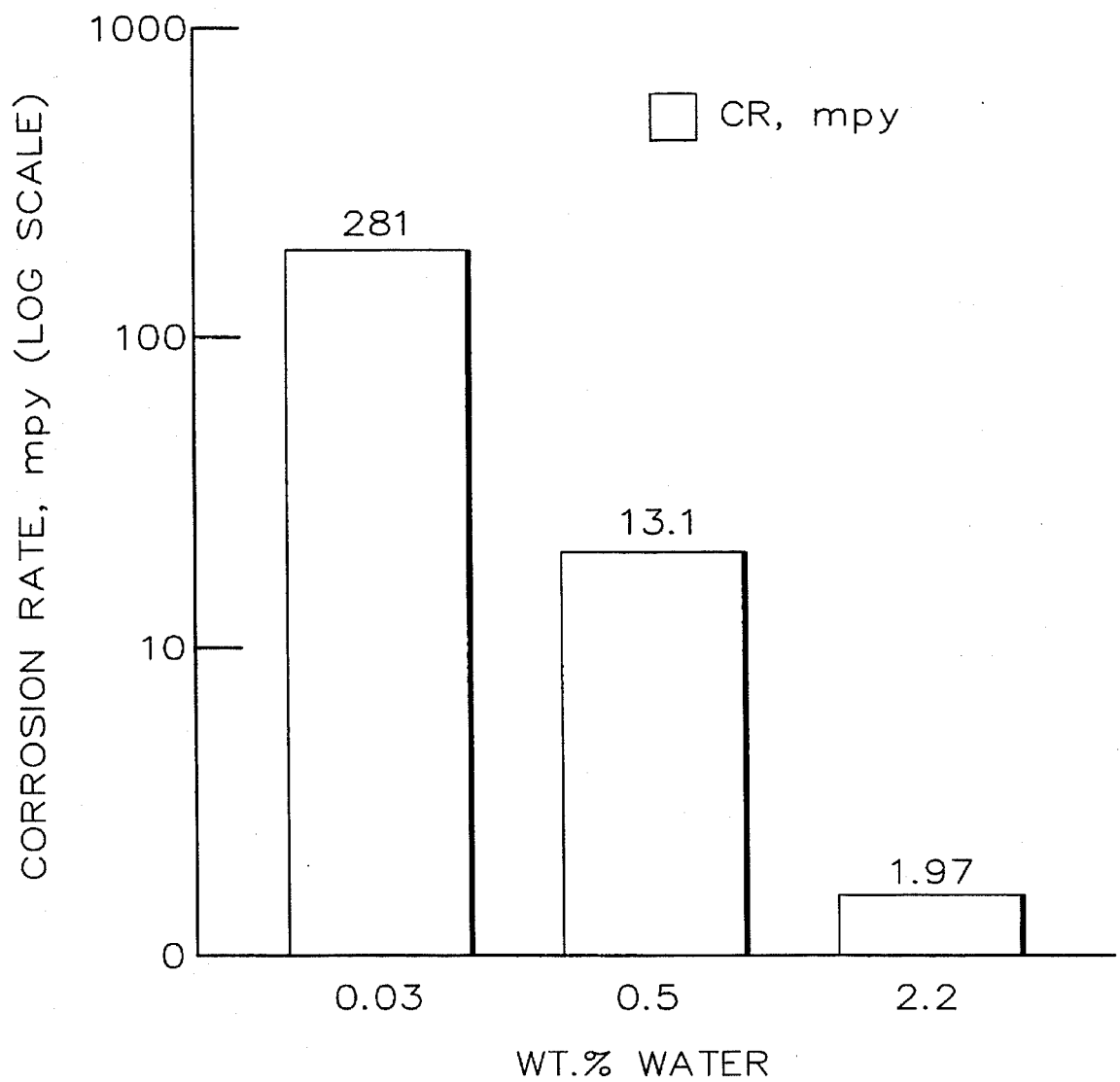
FIG. 1 is a bar diagram showing the corrosion rate of carbon steel in units of mils of corrosion per year for various water concentrations in a hydrogen fluoride and sulfolane mixture.

The invention provides an isoparaffin:olefin alkylation catalyst which provides commercially useful alkylation activity without aggressively corroding carbon steel process equipment. Most importantly, because the catalyst composition of the invention is compatible with carbon steel process equipment, the catalyst composition of the invention may be substituted for concentrated HF in an existing isoparaffin:olefin alkylation process unit without substantial equipment modifications.

The novel composition of the present invention is suitable for use as an alkylation catalyst and can comprise, consist of, or consist essentially of a hydrogen halide component, a sulfone component and water.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form or in aqueous form; provided that, the amount of water contained in the aqueous solution is not such that the ultimate water concentration in the alkylation catalyst or composition exceeds the desirable ranges described herein.

The sulfone component is an important and critical component of the catalyst composition because of the several functions it serves and because of the unexpected physical properties that it imparts to the catalyst composition. One important function of the presence of the sulfone component in the composition is its vapor pressure depressant or lowering effect upon the overall catalyst composition. It is an essential aspect of this invention for the sulfone component to be soluble in the hydrogen halide component and for the sulfone component to be essentially immiscible with olefin and paraffin hydrocarbons so as to permit easy separation of the hydrocarbons from the catalyst composition. Also, it is essential for the presence of the sulfone component to have a minimal impact upon an alkylation reaction selectivity and activity.

Generally, those skilled in the art of hydrogen fluoride catalyzed olefin alkylation processing have known that to obtain the highest quality of alkylate from the aforementioned olefin alkylation process, it is essential for the hydrogen fluoride catalyst to be as free from contaminating compounds as is feasible. It is generally known that small amounts of other compounds contained in the hydrogen fluoride catalyst of an olefin alkylation process can have detrimental effects upon product alkylate quality by negatively affecting the selectivity of the alkylation reaction toward the production of a more desirable end-product; such as, for example, trimethylpentanes (TMP) in the case of the alkylation of butylenes by isobutane. It is further known to those skilled in the art that small amounts of components contained in a hydrogen fluoride alkylation catalyst can have a negative impact upon its activity toward the alkylation of olefins. Based upon the known effects of hydrogen fluoride catalyst contaminants upon the activity and selectivity of the alkylation process toward the production of high quality alkylate, one skilled in the art would expect that the addition of small to large amounts of a sulfone compound to a hydrogen fluoride catalyst would have an enormously detrimental effect upon its catalytic performance. However, it has been discovered that the presence of small quantities of a sulfone compound in combination with hydrogen fluoride will have little negative impact on the performance of the resultant mixture as an alkylation catalyst; but, it is further unexpected that instead of having a detrimental impact upon the catalytic performance, a small concentration in an amount less than about 30 weight percent of a sulfone component in combination with the hydrogen fluoride can enhance the performance of the resultant composition as an alkylation process catalyst.

Therefore, to take advantage of the vapor pressure depressant effects of the sulfone compound, it is desirable to utilize the sulfone in the catalyst mixture in an amount wherein the weight ratio of the hydrogen halide to the sulfone is in the range of from about 1:1 to about 40:1. A weight ratio of hydrogen halide to sulfone in the catalyst mixture of less than 1:1 has such a significantly negative impact upon alkylate quality when the composition is utilized as an alkylation reaction catalyst that the composition becomes commercially ineffective as a catalyst. Thus, a 1:1 weight ratio of hydrogen halide to sulfone in the catalyst mixture becomes a critical lower limit for this ratio. In the situation where both vapor pressure depression and improved catalytic activity and/or selectivity are desired, the composition that works best in the alkylation of olefins will have a weight ratio of hydrogen halide to sulfone in the range of from about 1:1 to about 40:1. To achieve optimal benefits from the catalyst composition, the preferred catalyst mixture should have a weight ratio of hydrogen halide to sulfone in the range of from about 2.3:1 to about 19:1 and, more preferably, the weight ratio shall range from 3:1 to 9:1.

The sulfones suitable for use in this invention are the sulfones of the general formula

R—SO—R' wherein R and R'0 are monovalent hydrocarbon alkyl or aryl substituents, each containing from 1 to 8 carbon atoms. Examples of such substituents include dimethylsulfone, di n-propylsulfone, diphenylsulfone, ethylmethyl- sulfone, and the alicyclic sulfones wherein the $SO_2$ group is bonded to a hydrocarbon ring. In such a case, R and R'0 are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

This novel alkylation catalyst composition solves many of the problems that herebefore have been encountered in typical alkylation processes that use hydrofluoric acid as an alkylation catalyst. For instance, this novel catalyst composition has a significantly lower vapor pressure than that of the standard hydrofluoric acid alkylation catalyst. The advantage from using an alkylation catalyst having a much lower vapor pressure than that of hydrofluoric acid is that a lesser amount of the acid catalyst will vaporize and enter into the atmosphere in cases where the catalyst is exposed to the atmosphere. In particular, when making a comparison between the novel catalyst composition and hydrofluoric acid, one notices a significant difference in the vapor pressures of the two catalysts. Since hydrofluoric acid has a substantial vapor pressure at typical atmospheric or ambient conditions, it is often in a vapor state when it is exposed to the atmosphere; thus, this vapor pressure makes it more difficult to control and contain in cases where it is exposed to the atmosphere.

The novel catalyst composition as described herein, solves many of the problems associated with the use of hydrofluoric acid as a catalyst since it provides the benefit of having a lower vapor pressure at ambient conditions than that of hydrofluoric acid. But, in addition to the benefit of having a lower vapor pressure at ambient conditions, the novel catalyst composition further can be utilized in typical alkylation processes to provide practical reaction rates at low operating pressures and low operating temperatures to produce a high quality alkylate product which is suitable for use as a blending component of gasoline motor fuel. A further benefit from the novel catalyst composition is that it is easier to handle commercially than hydrofluoric acid.

In spite of the many advantages from the use of the novel composition comprising, consisting of, or consisting essentially of a hydrogen halide component and a sulfone component, the composition can have a corrosive effect upon metal when it comes into contact with such metal, for example, when the composition is utilized in an alkylation process system having carbon steel pressure vessels, piping, equipment and other appurtenances. As earlier mentioned herein, those skilled in the art of alkylation technology have known that small concentrations of contaminants contained in an alkylation catalyst can accelerate the rate at which corrosion occurs when the catalyst is contacted with a metal over that which would occur when the catalyst is free of a contaminant. One example of this phenomenon is in the case where anhydrous hydrogen fluoride is utilized as an alkylation catalyst. In this instance, it has been known that aqueous hydrogen fluoride is a more corrosive medium than anhydrous hydrogen fluoride and that the greater the concentration of water contained in the aqueous hydrogen fluoride, the more corrosive is its nature when utilized in a carbon steel alkylation process system. An additional problem traditionally caused by the presence of water in the catalyst system of an alkylation process is that it has a negative impact upon the ultimate alkylation end-product. Therefore, because of the aforementioned reasons, it is exceedingly unexpected for the presence of water in an alkylation catalyst composition or system, as contemplated by this invention, to have the effect of reducing or retarding the corrosive nature of the catalyst but without having a significant impact on an alkylate end-product.

Thus, this invention contemplates the incorporation of water into a catalyst system or composition containing a hydrogen halide and a sulfone in an amount sufficient to inhibit corrosion of a metal when the catalyst system or composition comes into contact with the metal. Generally, it has been discovered that the concentration of the water in the catalyst system can range from about 0.25 to about 10.0 weight percent with the weight percent of the water being based on the sum weight of the hydrogen halide and sulfone components. The ranges of the weight ratio of the hydrogen halide component to the sulfone component in the catalyst are those previously described herein. It is preferred for the water to be present in the catalyst system in an amount in the range of from about 0.5 to about 10 weight percent and, most preferably, the water can be present in the range of from 1.0 to 5 weight percent.

Alkylation processes contemplated by the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8.5 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are generally in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone in the presence of the alkylation catalyst of the present invention should generally be sufficient to provide essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin can be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The sulfolane component of the alkylation catalyst composition may be added by injection directly into the alkylation process unit, or may be mixed with the hydrocarbon charge, or may be mixed with the fresh and/or the circulating acid catalyst component, or with a stream of mixed acid/additive catalyst. Downstream from the alkylation reaction zone, the sulfolane is preferably separated from the alkylate product stream, mixed with fresh and/or circulating acid and/or circulating acid/additive catalyst mixture, and recycled to the alkylation reaction zone.

Figure 3:
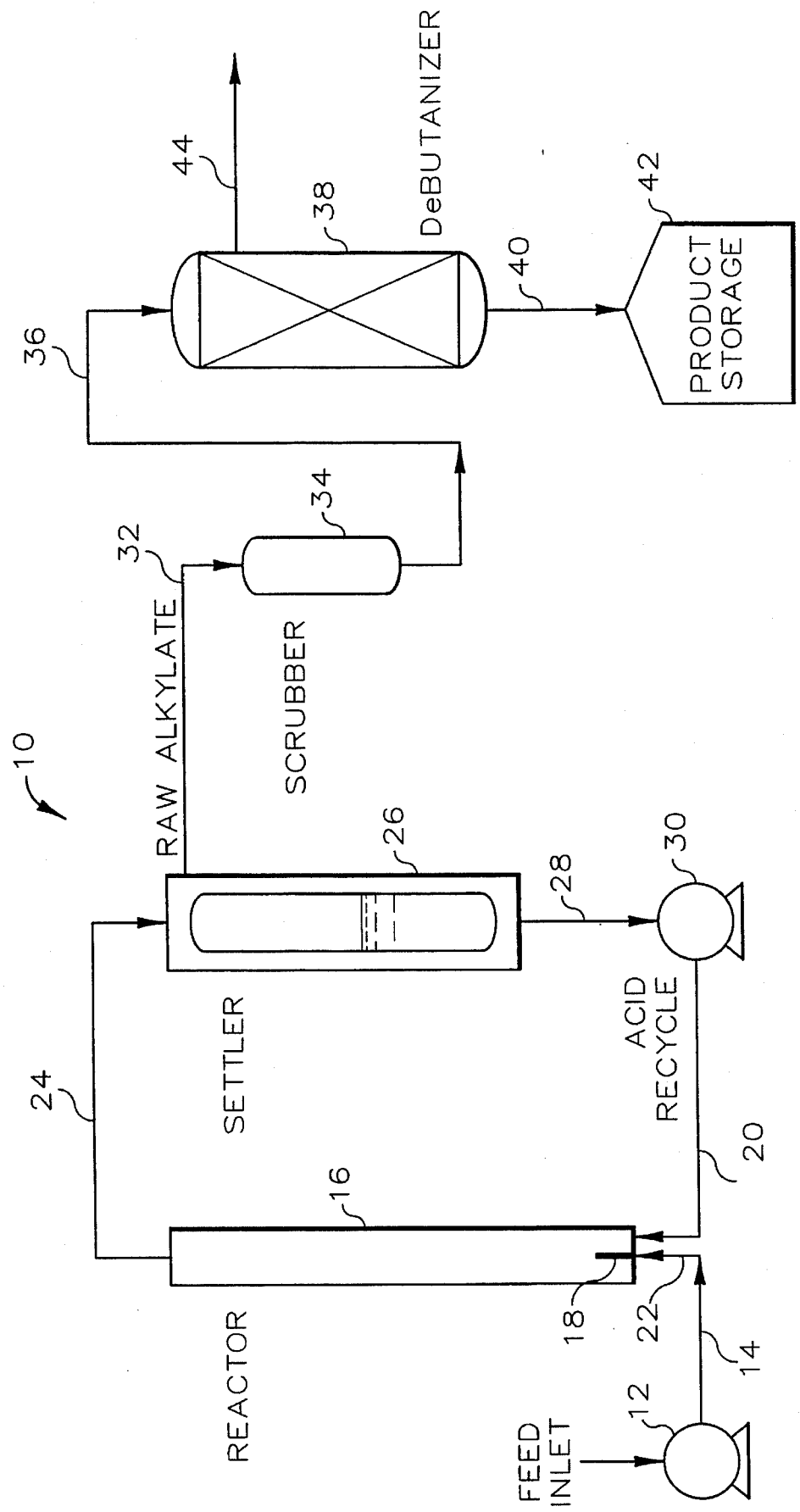
FIG. 3 is a schematic flow diagram of one embodiment of an alkylation process that utilizes the novel catalyst composition described herein.

Now referring to FIG. 3, there is presented a schematic flow diagram of a riser-reactor process system 10 that can be used in the alkylation of olefins by isoparaffins. Pressure and kinetic energies are imparted to a hydrocarbon mixture, or hydrocarbon feed, comprising olefin and isoparaffin hydrocarbons, by pump 12 that is utilized to charge the feed via conduit 14 to reactor vessel 16. Reactor vessel 16 defines an alkylation reaction zone wherein the hydrocarbon feed is reacted by contact with the novel catalysts as described herein. Upon entering reactor vessel 16, the hydrocarbon feed is intimately mixed with the novel catalyst by any suitable mixing means 18 for dispersing the hydrocarbon feed into the catalyst. Suitable mixing means 18 can include, but are not limited to jets, nozzles, porous thimbles and the like. The catalyst is fed to reactor vessel 16 via conduit 20 and the hydrocarbon feed mixture is charged to reactor vessel 16 through mixing means 18 via conduit 22.

The resultant reactor effluent from reactor vessel 16 passes by way of conduit 24 to settler vessel 26 which defines a separation zone and provides means for separating the reactor effluent into a hydrocarbon phase and a catalyst phase. The catalyst is then taken from settler vessel 26 by way of conduit 28 to pump 30. Pump 30 provides means for imparting both kinetic energy and pressure energy to the catalyst phase taken from settler vessel 26 and feeding, or recycling, it to mixing means 18 via conduit 20. The hydrocarbon phase is taken from settler vessel 26 by way of conduit 32 to scrubber vessel 34, which defines a scrubbing zone, or removal zone, and provides removal means for removing trace quantities of acid catalyst contained within the hydrocarbon phase to produce a scrubbed hydrocarbon phase. Any suitable removal means can be used; however, one preferred method is to contact the hydrocarbon phase, containing a trace concentration of acid catalyst, with a bed of alumina material contained within scrubber vessel 34.

The scrubbed hydrocarbon phase is passed by way of conduit 36 to debutanizer 38, which defines a separation zone and provides separation means for separating hydrocarbons having more than four carbon atoms and hydrocarbons having less than five carbon atoms. The hydrocarbons having more than four carbon atoms pass via conduit 40 to product storage vessel 42. The hydrocarbons having less than five carbon atoms pass by way of conduit 44 to downstream processing.

The following examples demonstrate the advantages of the present invention and the effectiveness of the sulfolane-containing catalyst composition of the invention for catalyzing isoparaffin:olefin alkylation. These examples are by way of illustration only, and are not intended as limitations upon the invention as set out in the appended claims.

EXAMPLE I

This example describes the experimental method used to determine the corrosivity of an HF and sulfolane mixture towards carbon steel and the corrosivity of the mixture towards carbon steel when various concentration levels of water are used to thus demonstrate the effectiveness of water as a corrosion inhibitor. Two different test procedures were employed in determining the corrosion rates of carbon steel coupons. The following described Procedure 1 was used for tests 1–20, and procedure 2 was used for tests 21–23.

Procedure 1

A single carbon steel coupon of dimensions 1×0.25×0.07 inches weighing 1.5–2.0 g was accurately weighed and measured. This coupon was then suspended in either a double-ended, Teflon-lined monel sample cylinder of 150 mL capacity or a stainless steel sample cylinder of 75 ml capacity by using Teflon string through a hole in the coupon. The position of the coupon was such that the coupon would remain submerged in the test solution when the cylinder was placed in an upright position.

The cylinder was evacuated, charged with the test solution and capped. Heat tape and insulation were wrapped around the cylinder and the cylinder was placed in an upright position on an orbital shaker set to rotate at 60 rpm. Temperature was maintained at 115° F.

At the conclusion of the test, the cylinder was cooled to room temperature and emptied of its contents. The coupon was then carefully removed from the cylinder and rinsed gently with sodium bicarbonate solution, water and acetone. After air drying, the coupon was dipped into an uninhibited HCl solution for 20 seconds, removed, washed again and gently polished with fine steel wool. The coupon was then weighed and measured accurately. Corrosion was calculated in mils per year, whereby a "mil" is defined as 0.001 inch.

Procedure 2

This procedure is similar to that of procedure 1 with the exception that a 300 cc hastelloy C autoclave replaced the monel or stainless steel sample cylinder as the test vessel. One coupon identical to those used above was suspended in the autoclave by Teflon string so as to eliminate the possibility for metal-metal contact while ensuring the coupon would be submerged completely in the test solution. After suspending the coupon, the test solution was added.

Temperature was maintained by a constant temperature bath circulating through internal autoclave heating coils; the test solution was stirred at a rate of 500 rpm throughout the trial.

Upon completion of the test, the test solution was drained and the coupon was treated as in procedure 1.

EXAMPLE II

Figure 2:
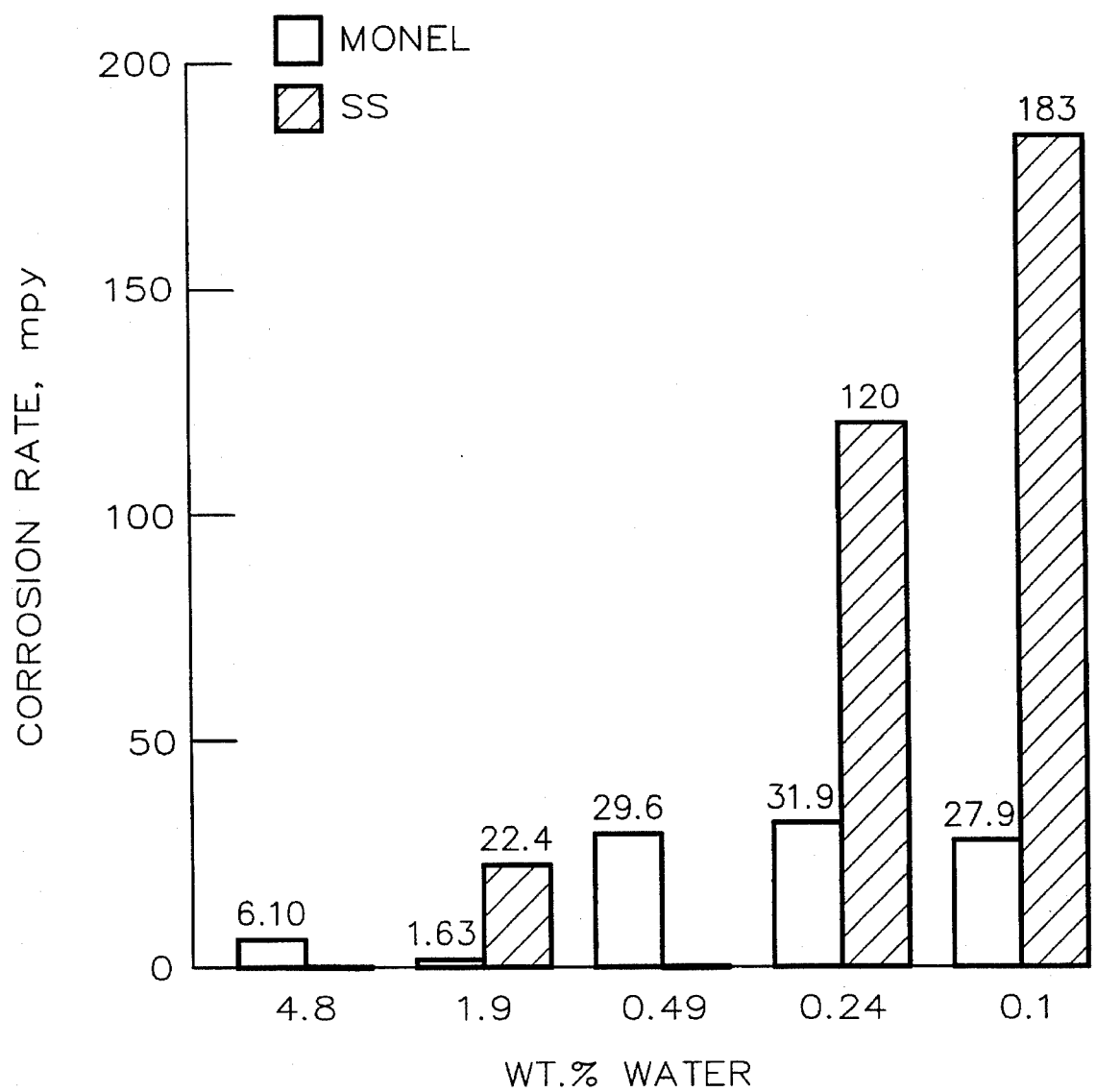
FIG. 2 is a bar diagram comparing the corrosion rate of carbon steel for various water concentrations in a hydrogen fluoride and sulfolane mixture in different test vessels.

This example presents data obtained by the previously described experimental method of Example I. The data presented in Table I demonstrate, unexpectedly, that the presence of water in an HF and sulfolane mixture has no detrimental effect on the corrosivity of the mixture towards carbon steel and that, in fact, the presence of small quantities of water in the mixture has an inhibitive effect upon its corrosive nature. FIGS. 1 and 2 are bar diagrams which present some of the corrosion data obtained by the method of Example I. These diagrams clearly illustrate that the presence of water in the HF and sulfolane mixture has a corrosion inhibitory effect when the mixture is contacted with metal.

TABLE I

HF/Sulfolane Carbon Steel Corrosion Testing Summary

| | Test Medium | | | Conditions | | |
|---|---|---|---|---|---|---|
| Test # | % HF | % Sulf. | % H₂O | Temp. °F. | Time, Days | Corr. Rate MPY |
| 1 | 76.5 | 23.5 | — | 120 | 17 | 7.84 |
| 2 | 71.4 | 27.1 | 1.5 | 115 | 15 | 3.06 |
| 3 | 68.9 | 25.5 | 5.6 | 115 | 15 | 5.06 |
| 4 | 61.6 | 38.4 | — | 115 | 15 | 17.8 |
| 5 | 58.8 | 36.4 | 4.8 | 115 | 15 | 6.10 |
| 6 | 63.2 | 36.8 | — | 115 | 17 | 192 |
| 7 | 59.8 | 38.3 | 1.9 | 115 | 17 | 1.63 |
| 8 | 100.0 | — | — | 115 | 17 | 1.24 |
| 9 | 96.9 | — | 3.1 | 115 | 17 | 0.97 |
| 11 | 58.2 | 38.8 | 2.0 | 85 | 4 | 22.4 |
| 12 | 61.2 | 38.8 | 0.25 | 85 | 4 | 120 |
| 13 | 64.8 | 35.2 | 0.085 | 85 | 4 | 183 |
| 14 | 59.8 | 40.1 | 0.100 | 115 | 7 | 27.9 |
| 15 | 61.3 | 38.5 | 0.241 | 115 | 7 | 31.9 |
| 16 | 61.6 | 37.9 | 0.488 | 115 | 7 | 29.6 |
| 17 | 63.5 | 36.5 | 0.036 | 115 | 5 | 59.8 |
| 18 | 59.8 | 40.1 | 0.12 | 115 | 6 | 50.5 |
| 19 | 61.7 | 38.2 | 0.12 | 115 | 6 | 31.9 |
| 20 | 62.3 | 37.6 | 0.037 | 115 | 5 | 9.25 |
| 21 | 60.3 | 39.6 | 0.03 | 115 | 4 | 281 |
| 22 | 55.3 | 42.5 | 2.2 | 115 | 5 | 1.97 |
| 23 | 60.1 | 39.4 | 0.5 | 115 | 5 | 13.1 |

EXAMPLE III

This example describes the method used to evaluate liquid catalysts mixtures comprising hydrogen fluoride, sulfolane and water as catalysts for the alkylation of mono-olefins by isobutane. Data are presented demonstrating the unexpected improvement in alkylate quality from the addition of small amounts of water to the hydrogen fluoride and sulfolane catalyst.

HF, sulfolane and water (60 wt. % HF, 38 wt. % sulfolane and 2 wt. % water) and HF and sulfolane (60 wt. % HF and 40 wt. % sulfolane) mixtures were evaluated for alkylation performance in the riser-reactor process system depicted in the schematic flow diagram of FIG. 3. In a typical reaction, the feed, a 10:1 isobutane:2-butenes feed, was contacted with the catalyst via a spray nozzle of 0.01 inch diameter orifice at a feed rate of 300 mL/hour. Temperature was maintained at 90° F. by circulating coolant from a constant temperature bath through a jacket surrounding the reactor. Reactor contents were maintained in the liquid phase by keeping the pressure at 100 psig. The contents of the reactor flowed from the reactor into the settler where phase separation occurred. Hydrocarbon was then collected and isolated for alkylate quality evaluation by gas chromatography; the acid phase recirculated to the reactor by way of a gear pump at a rate of approximately 700–750 mL/hour. Catalyst activity was observed to reach a maximum, followed by a slow decline throughout the reaction. No attempt was made to regenerate the catalyst or maintain catalyst activity in any of the runs cited, although it is known that replacement of small amounts of catalyst and/or removal of acid soluble oil byproducts would be sufficient to maintain catalyst life indefinitely.

Figure 4:
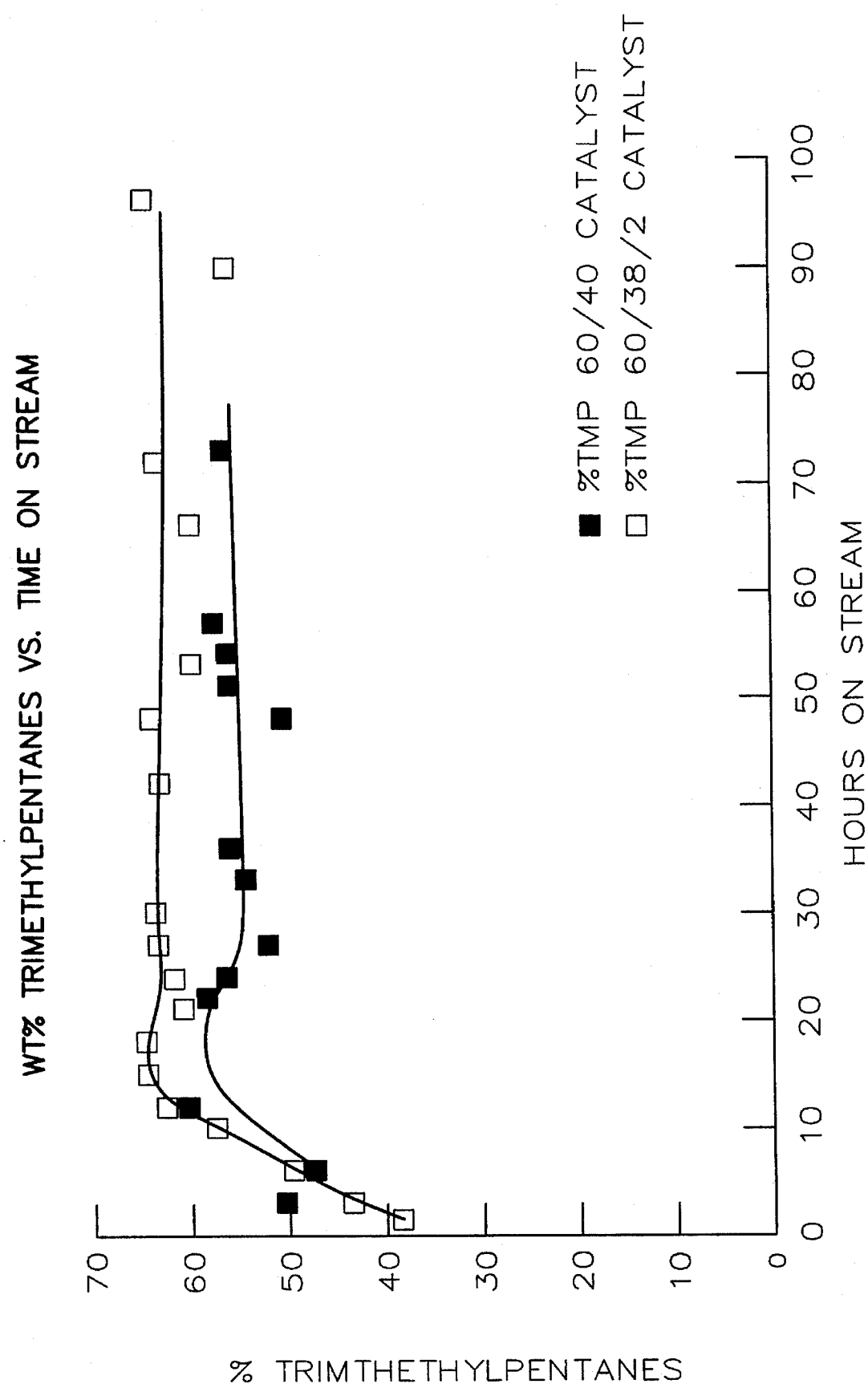
FIG. 4 is a graphical diagram comparing the alkylate quality produced by the alkylation of butenes by isobutane utilizing a catalyst composition comprising hydrogen fluoride and sulfolane with that produced with the catalyst composition additionally containing water.

The data presented in Tables II and III were obtained by using the experimental method described in this Example III. The data show that the presence of water has no deleterious effect on alkylate quality with the alkylate having a suitably higher octane number which reflects a suitably high concentration of branched octane compounds in the alkylate. Table II presents the data obtained for the HF, sulfolane and water catalyst mixture and Table III presents data obtained for an HF and sulfolane catalyst mixture. FIG. 4 graphically presents some of the data provided in Tables II and III relating to the weight percent of trimethylpentanes contained in the alkylate product. The graphically depicted data clearly demonstrates the enhancement in alkylate quality that is obtainable from the addition of a small quantity of water to a sulfolane and HF catalyst mixture.

TABLE II

Alkylate Overview: 60/38/2 HF/Sulf/H20 + Ideal Feeds

| Time, hrs. | 1.5 | 3 | 6 | 10 | 12 | 15 | 18 | 21 | 24 |
|---|---|---|---|---|---|---|---|---|---|
| C5-7 | 17.30 | 15.16 | 12.19 | 9.42 | 6.94 | 7.46 | 8.44 | 7.21 | 7.25 |
| C8 | 49.56 | 54.84 | 61.84 | 69.48 | 74.73 | 75.99 | 78.64 | 71.30 | 72.66 |
| C9+ | 28.90 | 26.44 | 21.18 | 14.98 | 13.00 | 6.96 | 9.20 | 6.26 | 6.91 |
| TMP | 38.67 | 43.42 | 49.86 | 57.48 | 62.32 | 64.44 | 64.57 | 60.76 | 61.70 |
| DMH | 10.89 | 11.42 | 11.99 | 12.00 | 12.41 | 11.56 | 14.06 | 10.22 | 10.63 |
| TMP/DMH | 3.55 | 3.80 | 4.16 | 4.79 | 5.02 | 5.58 | 4.59 | 5.94 | 5.80 |
| R + M/2* | 89.9 | 90.4 | 91.4 | 92.5 | 93.0 | 93.9 | 92.6 | 93.9 | 93.1 |
| R-F | 0.00 | 0.00 | 0.00 | 0.00 | 0.00 | 0.00 | 0.00 | 0.00 | 0.00 |
| % Convert | 100.00 | 100.00 | 100.00 | 100.00 | 100.00 | 100.00 | 100.00 | 100.00 | 100.00 |

| Time, hrs | 27 | 30 | 42 | 48 | 53 | 66 | 72 | 90 | 96 |
|---|---|---|---|---|---|---|---|---|---|
| C5-7 | 8.07 | 7.81 | 8.67 | 7.88 | 9.32 | 8.89 | 8.00 | 9.28 | 6.92 |
| C8 | 74.93 | 75.83 | 75.36 | 77.04 | 71.68 | 72.48 | 76.03 | 68.38 | 78.07 |
| C9+ | 6.01 | 8.29 | 8.27 | 8.96 | 8.47 | 10.87 | 11.03 | 12.00 | 12.99 |
| TMP | 63.20 | 63.67 | 63.05 | 64.03 | 59.98 | 59.98 | 63.21 | 55.94 | 64.53 |
| DMH | 11.74 | 12.16 | 12.31 | 13.01 | 11.70 | 12.51 | 12.82 | 12.44 | 13.54 |
| TMP/DMH | 5.38 | 5.24 | 5.12 | 4.92 | 5.13 | 4.80 | 4.93 | 4.50 | 4.77 |
| R + M/2* | 93.8 | 93.5 | 93.4 | 93.4 | 93.3 | 92.9 | 93.0 | 92.4 | 92.7 |

TABLE II-continued

| Alkylate Overview: 60/38/2 HF/Sulf/H2O + Ideal Feeds | | | | | | | | | |
|---|---|---|---|---|---|---|---|---|---|
| R-F | 0.00 | 0.00 | 0.09 | 0.07 | 0.00 | 0.15 | 0.00 | 0.17 | 0.00 |
| % Convert | 100.00 | 100.00 | 100.00 | 100.00 | 100.00 | 100.00 | 100.00 | 100.00 | 100.00 |

*Calculated

TABLE III

| | Total Product Stream Alkylates: 60/40 HF/Sulfolane + Ideal Feeds | | | | | | | | | | | | |
|---|---|---|---|---|---|---|---|---|---|---|---|---|---|
| Time, hrs. | 3 | 6 | 12 | 22 | 24 | 27 | 33 | 36 | 48 | 51 | 54 | 57 | 73 |
| C5-7 | 6.30 | 9.62 | 5.93 | 6.52 | 7.83 | 7.37 | 7.93 | 7.65 | 9.74 | 8.25 | 7.86 | 7.19 | 7.10 |
| C8 | 59.57 | 54.39 | 74.58 | 69.73 | 67.55 | 62.14 | 65.07 | 67.35 | 60.44 | 67.19 | 67.18 | 68.95 | 68.02 |
| C9+ | 14.03 | 4.24 | 9.90 | 12.42 | 13.05 | 14.87 | 11.02 | 14.19 | 9.91 | 12.37 | 11.86 | 13.77 | 15.63 |
| TMP | 50.32 | 47.25 | 60.38 | 58.26 | 56.38 | 51.95 | 54.27 | 56.06 | 50.45 | 55.96 | 56.08 | 57.63 | 56.51 |
| DMH | 9.25 | 7.14 | 14.20 | 11.47 | 11.16 | 10.18 | 10.81 | 11.29 | 9.99 | 11.23 | 11.11 | 11.31 | 11.52 |
| TMP/DMH | 5.44 | 6.62 | 4.25 | 5.08 | 5.05 | 5.10 | 5.02 | 4.96 | 5.05 | 4.99 | 5.05 | 5.09 | 4.91 |
| R + M/2* | 93.0 | 94.2 | 93.0 | 93.1 | 92.9 | 92.6 | 93.0 | 92.7 | 92.9 | 92.8 | 93.0 | 92.8 | 92.5 |
| R-F | 0.41 | 0.86 | 0.36 | 0.41 | 0.41 | 0.37 | 0.54 | 0.45 | 0.75 | 0.55 | 0.51 | 0.38 | 0.50 |
| % Convert | 100.00 | 100.00 | 100.00 | 100.00 | 100.00 | 100.00 | 100.00 | 100.00 | 100.00 | 100.00 | 100.00 | 100.00 | 100.00 |

*Calculated

EXAMPLE IV

This example describes the experimental method used to determine the vapor pressure of various hydrogen fluoride and sulfolane mixtures and to present vapor pressure data for such mixtures demonstrating the effectiveness of sulfolane as a vapor pressure depressant.

A 100 mL monel bomb was dried and evacuated, followed by the addition of a prescribed amount of anhydrous hydrogen fluoride. A specific amount of sulfolane was then added to the bomb. Once the bomb achieved the desired temperature, the pressure within the bomb was recorded. The vapor pressure was assumed to be that of HF vapor alone (sulfolane has a boiling point of 283° C.). Table IV presents a portion of the vapor pressure data obtained by this experimental method and illustrates the change in vapor pressure of the novel hydrogen fluoride and sulfolane catalyst mixture as a function of the weight percent sulfolane in the catalyst mixture.

TABLE IV

| Vapor Pressure of HF/sulfolane Mixtures at 30° C. | |
|---|---|
| Wt. % Sulfolane | Vapor Pressure (Torr) |
| 0.00 | 1086 |
| 3.82 | 1044 |
| 4.75 | 1032 |
| 7.36 | 1021 |
| 7.65 | 1004 |
| 13.01 | 972 |
| 16.57 | 946 |
| 19.90 | 897 |
| 19.95 | 902 |
| 24.11 | 862 |
| 26.95 | 819 |
| 29.01 | 794 |
| 30.02 | 812 |
| 36.70 | 680 |
| 55.40 | 413 |
| 71.96 | 187 |
| 83.91 | 74 |

EXAMPLE V

This example describes the method which utilizes batch reactions to test the feasibility of using a hydrogen fluoride and sulfolane mixture as a catalyst for the alkylation of mono-olefins by isoparaffins. Data are presented to demonstrate the unexpectedly improved properties of the alkylate product from such a catalytic process and to demonstrate that for certain concentration ranges the catalyst mixture unexpectedly provides a good quality alkylate.

HF/sulfolane mixtures were evaluated for alkylation performance in batch reactions at 90° F. In a typical trial, the desired amount of sulfolane was added to a 300 mL monel autoclave under a blanket of nitrogen. Anhydrous HF was then introduced into the autoclave and heated to 90° F. with stirring at 500 RPM. The stirring was then increased to 2500 RPM, and an 8.5:1 isobutane:2-butenes mixture was added with nitrogen back pressure at a rate of 100 mL/min. at a pressure of 150–200 psig. After 5 minutes, the stirring was stopped, followed by the transfer of the reactor contents to a Jerguson gauge for phase separation. The hydrocarbon product was then characterized by gas chromatography.

The data presented in Table V were obtained by using the experimental method described in this Example V.

TABLE V

| Batch Results, Anhydrous HF/Sulfolane | | | | | | |
|---|---|---|---|---|---|---|
| | Test Samples | | | | | |
| | No. 1 | No. 2 | No. 3 | No. 4 | No. 5 | No. 6 |
| mL sulfolane | 0.00 | 13.00 | 28.00 | 38.00 | 50.00 | 50.00 |
| mL HF | 100.00 | 93.50 | 86.00 | 81.00 | 75.00 | 50.00 |
| mL Feed | 100.00 | 93.50 | 86.00 | 81.00 | 75.00 | 100.00 |
| wt. % sulfolane | 0.00 | 15.09 | 29.39 | 37.49 | 46.02 | 56.11 |
| % TMP | 65.40 | 71.28 | 67.29 | 57.14 | 52.21 | 20.45 |
| % DMH | 9.63 | 9.02 | 10.52 | 11.90 | 12.28 | 1.58 |
| TMP:DMH | 6.79 | 7.90 | 6.40 | 4.80 | 4.25 | 12.97 |
| C9+ | 5.81 | 10.56 | 10.98 | 16.49 | 18.96 | 0.28 |
| Organic fluorides | 0.00 | 0.00 | 0.00 | 0.00 | 0.00 | 69.74 |

EXAMPLE VI

This example describes the steady state evaluation method for testing the feasibility of using a hydrogen fluoride and sulfolane mixture as a catalyst for the alkylation of mono-olefins by isoparaffins. Data are presented to demonstrate that for certain concentration ranges the catalyst mixture unexpectedly provides a good quality alkylate.

A reactor was constructed to enable steady state evaluation of HF/sulfolane alkylation catalysts using a 300 mL monel autoclave. A 10:1 isobutane:2-butenes feed was introduced into the autoclave with stirring at 2000 RPM at a rate of 600 mL/hour. The reactor effluent flowed into a monel Jerguson gauge for phase separation. The hydrocarbon phase was passed through alumina and collected, while the acid phase was recirculated to the reactor. Alkylate was evaluated by gas chromatography and by research and motor octane tests performed on test engines.

The data presented in Table VI was obtained by using the experimental method described in this Example VI.

TABLE VI

|  | 100% HF | 70/30 HF/sulfolane | 60/40 HF/sulfolane | 50/50 HF/sulfolane | 40/60 HF/sulfolane |
|---|---|---|---|---|---|
| C8 | 93.5 | 81.1 | 82.2 | 56.9 | 26.95 |
| TMP | 86.3 | 70.5 | 70.4 | 46.1 | 22.26 |
| DMH | 7.1 | 10.6 | 11.7 | 10.6 | 4.54 |
| TMP/DMH | 12.1 | 6.6 | 6.0 | 4.4 | 4.90 |
| C9+ | 3.4 | 3.9 | 8.1 | 23.1 | 36.32 |
| R + M/2 | 97.0 | 95.5 | 94.9 | 93.7 | NA |

EXAMPLE VII—COMPARATIVE

Example VII demonstrates the well-known effectiveness of anhydrous HF as an isoparaffin:olefin alkylation catalyst and is presented for comparison to evaluate the effectiveness of the alkylation catalyst composition of the present invention (Examples VIII–X.

Anhydrous HF (40 grams, obtained from Metheson Chemical Company of Bridgeport, N.J.) was condensed into a clean, dry autoclave (1000 cc). Isobutane (100 grams) was added, and the autoclave was stirred at 1500 rpm. The autoclave was brought to room temperature (22° C., 71° F.) and pressurized to 100 psig. A premixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. A 10°14 15° F. (5°–8° C.) temperature rise was observed during feed addition resulting in an average reaction temperature of 27°–30° C. (80°–85° F.). The autoclave was sampled (300 cc) immediately after feed addition was complete. The sample was flashed at room temperature and quenched with a chilled water trap. Samples of the liquid and gas products were analyzed by capillary GC (60 m DB-1 column). The results of Example VII are shown in the Table A below.

EXAMPLES VIII THROUGH X

The following procedure was followed for Examples VIII through X. In a typical experiment, 10 grams of sulfolane (tetramethylene sulfone, Phillips Petroleum Co.) was loaded into a clean, dry 1000 cc autoclave. Sulfolane was stored in a vacuum desiccator over $P_2O_5$ prior to use. The autoclave was sealed and cooled with liquid nitrogen. The autoclave was evacuated and 40 grams of anhydrous HF (Matheson) were condensed into the autoclave. The HF/sulfolane mixture was warmed to room temperature (71° F.). Isobutane (100 grams) was added to the mixture, the autoclave was pressurized to 100 psig and stirred at 1500 rpm. A premixed 10/1 wt/wt isobutane/2-butene feed (Matheson) was then introduced at 250 cc/hr. A 5°–10° F. temperature rise was typically observed during reaction. After two hours, feed addition was halted and a 300 cc liquid sample was obtained. The liquid sample was depressured through an ice cooled trap (filled with 50 cc of water) which was connected to a gas sampling bomb and wet test meter. The liquid alkylate product and gas sample were analyzed with a Varian 5000 gas chromatograph equipped with a 60 meter DB-1 capillary column.

Table A below lists the results with HF/sulfolane mixtures containing up to 50 wt % sulfolane in HF. With 20 wt % sulfolane in HF (125 moles HF per liter sulfolane), performance was comparable to pure HF. The ratio of high octane trimethylpentanes to lower octane dimethylhexanes (TMP/DMH) was 9.4 with 80/20 HF/sulfolane compared to 9.2 with pure HF. Performances diminished slightly upon adding 50 wt % sulfolane to HF (63 moles HF per liter of sulfolane). Alkylate with 50/50 HF/sulfolane catalyst had a TMP/DMH ratio of 6.5 and contained 11.8 wt % $C_9+$. A 40/60 HF/sulfolane catalyst (42 moles of HF per liter of sulfolane) showed no activity for alkylation. The only observed product was butyl fluoride formed by hydrofluorination of 2-butene feed. Thus, the useful concentration range for sulfolane in HF was shown to be below about 60 wt % in HF (greater than about 50 moles of HF per liter of sulfolane).

Figure 5A:
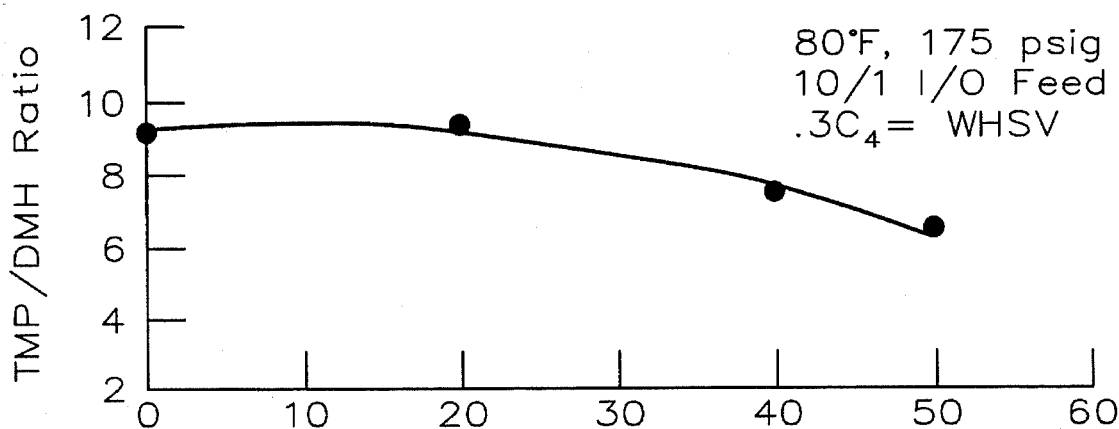
FIG. 5a is a plot of TMP/DMH ratio (trimethylpentane/ dimethylhexane) as a function of weight percent sulfolane in HF for isoparaffin:olefin alkylation at 80° F., 175 psig, 10/1 isobutane/butene ratio and olefin WHSV of 0.3 $hr^{-1}$.
Figure 5B:
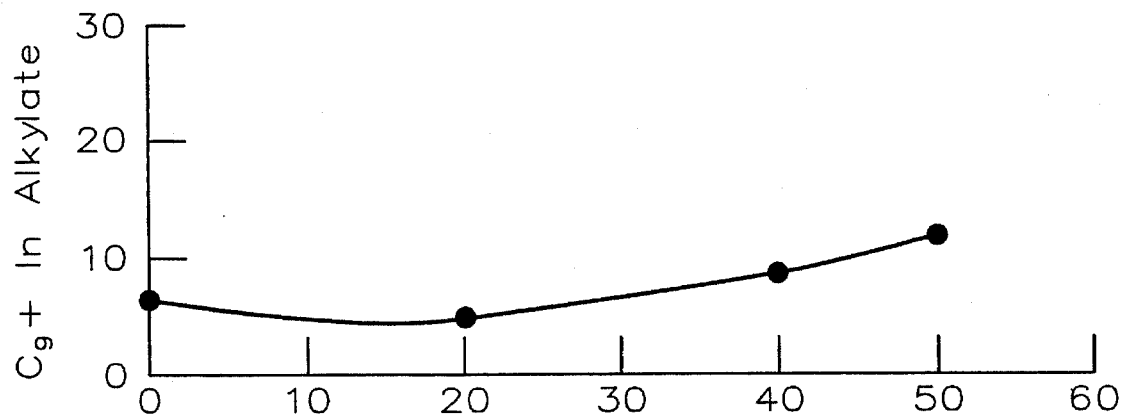
Figure 5C:
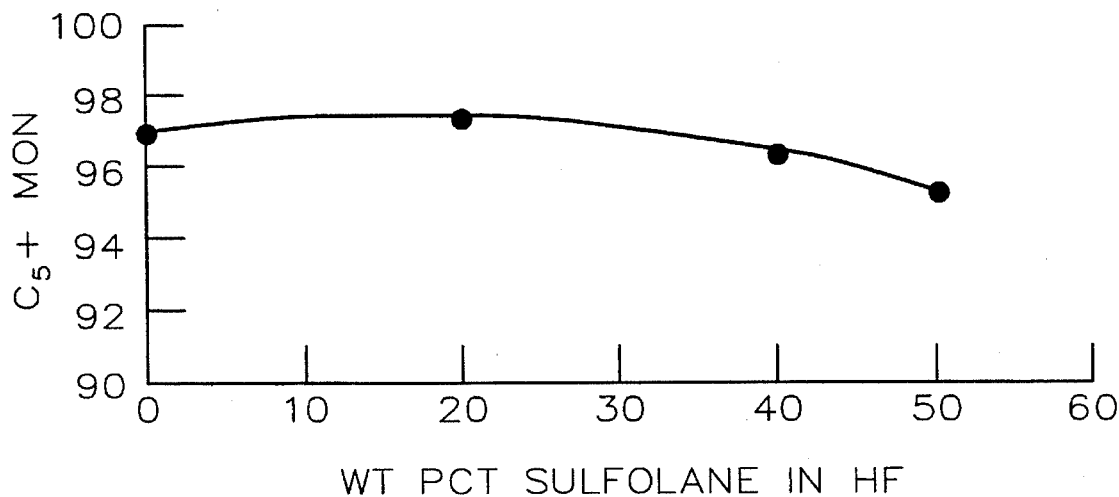
FIG. 5c is a plot of the MON (Motor Octane Number) of the $C_5+$ portion of the alkylate product produced by the isoparaffin:olefin reaction (described above with reference to FIG. 5a) as a function of weight percent sulfolane in HF.

HF/sulfolane catalyst performance is plotted as a function of sulfolane loading in FIGS. 5a, 5b, and 5c. Alkylate quality increased slightly upon adding 20 wt % sulfolane to HF ($C_5$+ MON 97.5 vs 97 for pure HF), then decreased with further sulfolane dilution. Activity for isoparaffin/olefin alkylation was not observed above about 50 wt % sulfolane in HF.

Figure 6:
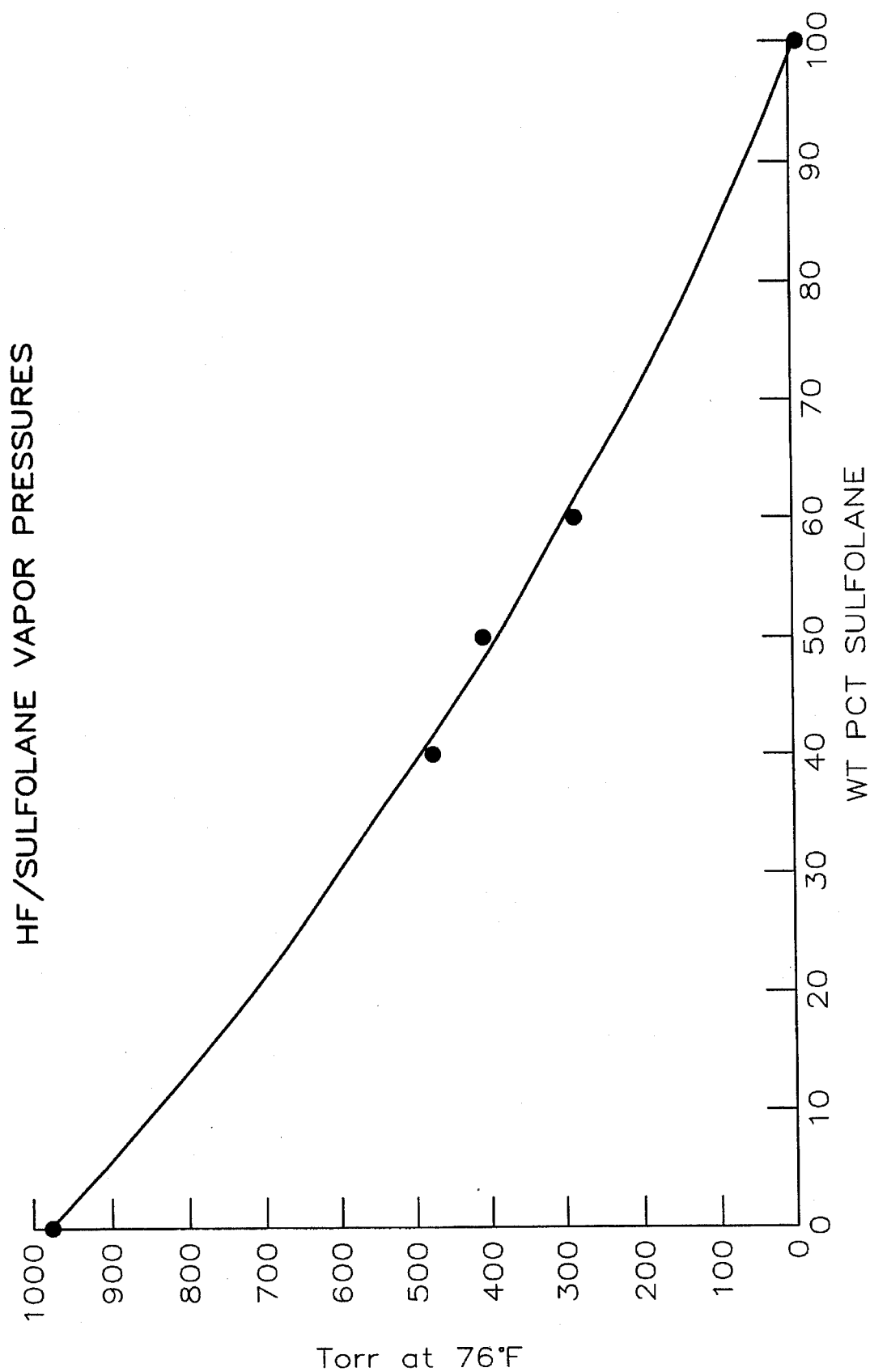
FIG. 6 is a plot of vapor pressure at 76° F. as a function of weight percent sulfolane in HF.

Vapor pressure (Torr) for HF/sulfolane mixtures are plotted as a function of sulfolane loading in FIG. 6, showing that diluting HF with sulfolane dramatically reduces vapor pressure.

TABLE A

| Example | VII | VIII | IX | X |
|---|---|---|---|---|
| Catalyst | HF | HF/Sulfolane (80/20) | HF/Sulfolane (60/40) | HF/Sulfolane (50/50) |
| Appearance | Fuming | Fuming | Liquid | Liquid |
| Alkylate Product wt % | | | | |
| $C_5$–$C_7$ | 5.5 | 4.7 | 5.9 | 8.3 |
| C8 | 88.1 | 89.3 | 85.5 | 79.9 |
| $C_9+$ | 6.4 | 6.0 | 8.6 | 11.8 |

TABLE A-continued

| Example | VII | VIII | IX | X |
|---|---|---|---|---|
| TMP/DMH | 9.2 | 9.4 | 7.5 | 6.5 |
| Olefin Conv., % | 99.9 | 100 | 98.0 | 98.8 |

EXAMPLES XI THROUGH XIII

HF/sulfolane mixtures were evaluated in a 1.5 foot long riser reactor having total volume of about 120 cc. The reactor was first filled with liquid isobutane at approximately 130 psig. Approximately 100 cc of premixed HF/sulfolane catalyst (70/30 wt/wt for Example XI, 60/40 wt/wt for Examples XII and XIII) was pressured into the reactor from the bottom, displacing a portion of the isobutane. The isobutane flow was maintained to keep the injection nozzle clear. Hydrocarbon residence time in the riser was approximately 6 seconds with a hydrocarbon drop diameter of about 300 microns. The olefin feed was obtained from a commercial HF alkylation process unit and was characterized by the following average composition:

| Component | Weight Percent |
|---|---|
| $C_3=$ | 12.4 |
| $C_4=$ | 81.8 |
| $C_5=$ | 5.8 |
| Total: | 100.0 |

Conversion conditions and results for Example XI are shown below in Table B.

TABLE B

| Example | XI | XII | XIII |
|---|---|---|---|
| Temperature °F. | 90 | 90 | 90 |
| Pressure, psig | 130 | 125 | 125 |
| Isoparaffin:Olefin Ratio in the Reactor Feed | 17.1 | 14.9 | 14.3 |
| Recovery, wt % | 100.5 | 99.6 | 94.1 |
| Conversion, wt % | 98.2 | 98.9 | 99.2 |
| C8 TMP/DMH | 5.0 | 5.9 | 5.8 |
| C8- olefins, wt % | | | |
| $C_5$s, wt % | 10.1 | 5.1 | 4.9 |
| $C_6$s, wt % | 3.5 | 3.2 | 3.2 |
| $C_7$s, wt % | 10.8 | 3.7 | 3.7 |
| $C_8$s, wt % | 61.6 | 74.9 | 74.4 |
| $C_9+$ | 12.9 | 12.5 | 13.2 |
| % TMP, wt % | | 64.0 | 63.5 |
| Yield, wt basis | 2.2 | 2.0 | 2.1 |
| R + O, raw | 97.1 | 96.9 | 97.0 |
| M + O, raw | 95.2 | 95.2 | 95.3 |

EXAMPLES XIV THROUGH XXI

Examples XIV–XXI examined the cloud-forming tendency of various mixtures of HF and sulfolane. The cloud-forming tendency was measured in terms of rainout, which is defined as the fraction of the released substance which falls to the ground within a defined area downwind from the point of release. For example, if 50% (weight) of a released substance falls to the ground within the defined area downwind from the point of release, the rainout is 50% (weight). Rainout is inversely related to cloud-forming tendency. In the event of an accidental release, material which precipitates or rains out can not pose a toxic hazard downwind from the site of the accidental release.

The HF and sulfolane were mixed in a 2-liter stirred autoclave which was fabricated from 316 stainless steel and contained a cooling/heating coil. The autoclave was pressured with nitrogen, and the contents of the autoclave were than released through a nozzle into a flow chamber. The liquid rainout was collected in trays and the material which carried over was scrubbed with water in accordance with the procedure set forth below.

The sulfolane was weighed and placed into the 2-liter autoclave. Anhydrous HF from a cylinder was measured using a calibrated Kel-F lined sight glass and pressured into the autoclave. The mount of HF used per run varied from 109 to 434 grams. Once the material was loaded into the autoclave, the wind velocity in the flow chamber was adjusted to the desired setting, usually about 0.9 m/s to simulate a typical release wind speed. Ambient humidity was used. The autoclave mixer was also turned on for several minutes to mix the contents. Water was placed into each of three dropout trays to catch the precipitated HF and sulfolane as well as to minimize evaporation losses. The water-filled trays were weighed to determine the pre-release base line weights.

The autoclave pressure was then set with nitrogen and the autoclave temperature was set by warm water or a Neslab cooler. The valve to the release orifice was then opened, and the material flowed into the chamber. The orifice diameter was 0.635 min. The dimensions of the flow chamber were approximately 40 inc. (length) by 12 in. (height) by 6 in. (depth). Because the release material had sufficient inertia to travel a greater length than the flow chamber, an impingement plate was placed at the end of the third tray. This plate was covered with steel wool to minimize splashing and to produce a good rainout of 98 percent with the base case water runs.

The liquid rainout was collected in the trays, with most of the material going into the tray closest to the impingement plate. The trays were then weighed to determine how much material rained-out. The data were then corrected for evaporation of water from the trays, liquid hold-up in the impingement plate pad, residual material in the autoclave, and material that adhered to the walls of the chamber.

Figure 7:
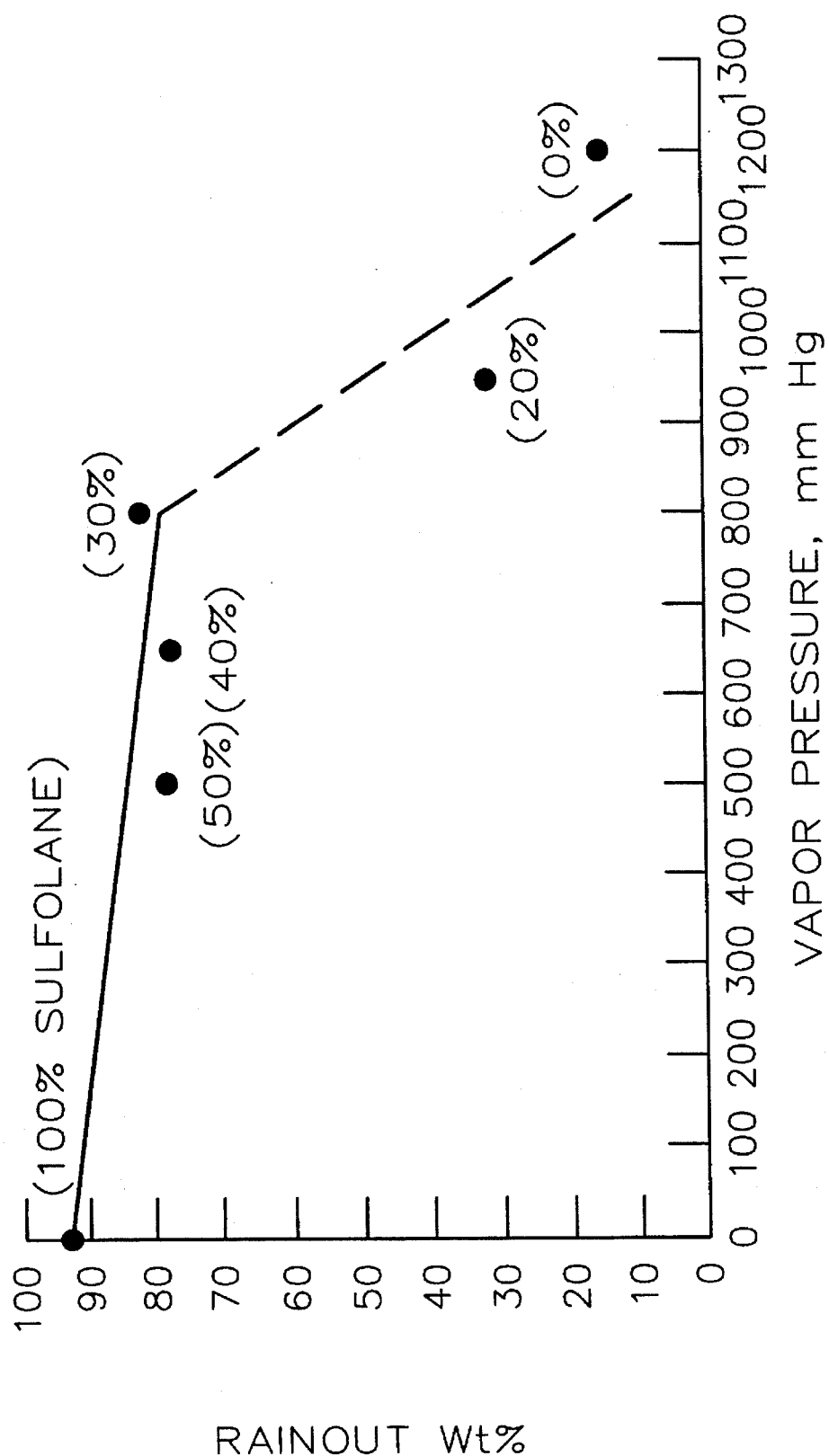
FIG. 7 is a plot of percent rainout (weight) as a function of vapor pressure for neat sulfolane, neat HF, and mixtures of HF and sulfolane containing from 20 to 80 percent sulfolane (weight).

The rainout data are shown below in Table C, and plotted in FIG. 7. Table C also lists the corresponding $C_5+$ alkylate TMP (trimethylpentane) content produced with each of the HF/sulfolane mixtures as isobutane:butene alkylation catalyst. These results show that the preferred catalyst composition provides excellent rainout (>70 wt. %) while also producing a high quality alkylate product.

TABLE C

Conditions: about 50 psig, 90° F., 0.635 mm orifice diameter.

| Example No. | Sulfolane (Wt %) | TMP (Wt %) | Rainout, wt % by Material Balance |
|---|---|---|---|
| XIV | 60 | * | |
| XV | 50 | | 76 |
| XVI | 50 | 69 | 76 |

TABLE C-continued

Conditions: about 50 psig, 90° F., 0.635 mm orifice diameter.

| Example No. | Sulfolane (Wt %) | TMP (Wt %) | Rainout, wt % by Material Balance |
| --- | --- | --- | --- |
| XVII | 50 | | 82 |
| XVIII | 40 | 73 | 76 |
| XIX | 40 | | 78 |
| XX | 30 | 78 | 81 |
| XXI | 20 | 80 | 32 |

* Less than 5 wt. %

EXAMPLE XXII THROUGH XXV—EXPERIMENTAL PROCEDURE

Mixtures of HF and sulfolane were evaluated for their corrosivity toward carbon steel in accordance with the following procedure.

Sulfolane (tetramethylene sulfone as received from Phillips Petroleum Company) was vacuum distilled twice from KOH and once from CaH. The dried sulfolane was stored in a vacuum desiccator over $P_2O_5$.

In a typical experiment, a carbon steel rod (5.25" long, 0.25"0 diameter) was attached to a Teflon connector to the top of a 300 cc stainless steel autoclave (fabricated by Autoclave Engineers, Inc.). Purified sulfolane (49.5 grams) and deionized water (1 gram) were added to the autoclave under a nitrogen atmosphere. The autoclave was sealed, cooled with liquid nitrogen, and evacuated with a rough vacuum. HF (60 grams, Matheson) was condensed into the autoclave. The cold autoclave was connected to a pilot unit equipped with a LPG feed system and acid scrubber. The autoclave was warmed to 85° F., pressurized to 100 psig with isobutane (Matheson), and stirred at 100 rpm. The contents were purged with 280 cc/hr of isobutane for 24 hours. The isobutane purge was removed and the autoclave was sealed for 150 hours at 85° F. and 100 psig. HF loss during the isobutane purge was estimated at 10 grams, thus the purged mixture sealed for 150 hours was roughly 50/49/1 wt./wt./wt. HF/sulfolane $H_2O$.

At the end of the corrosion experiment, the autoclave was vented through caustic scrubbers, and opened in a fume hood. The carbon steel rod was removed, rinsed with acetone and stored in a desiccator. The bottom portion (1 inch) of the carbon steel rod that was immersed in the HF/sulfolane catalyst developed a protective coating. The protective film was removed with a mechanical bead blaster to expose the non-corroded metal. The corrosion rate was determined from the measured decrease in rod thickness.

Figure 8:
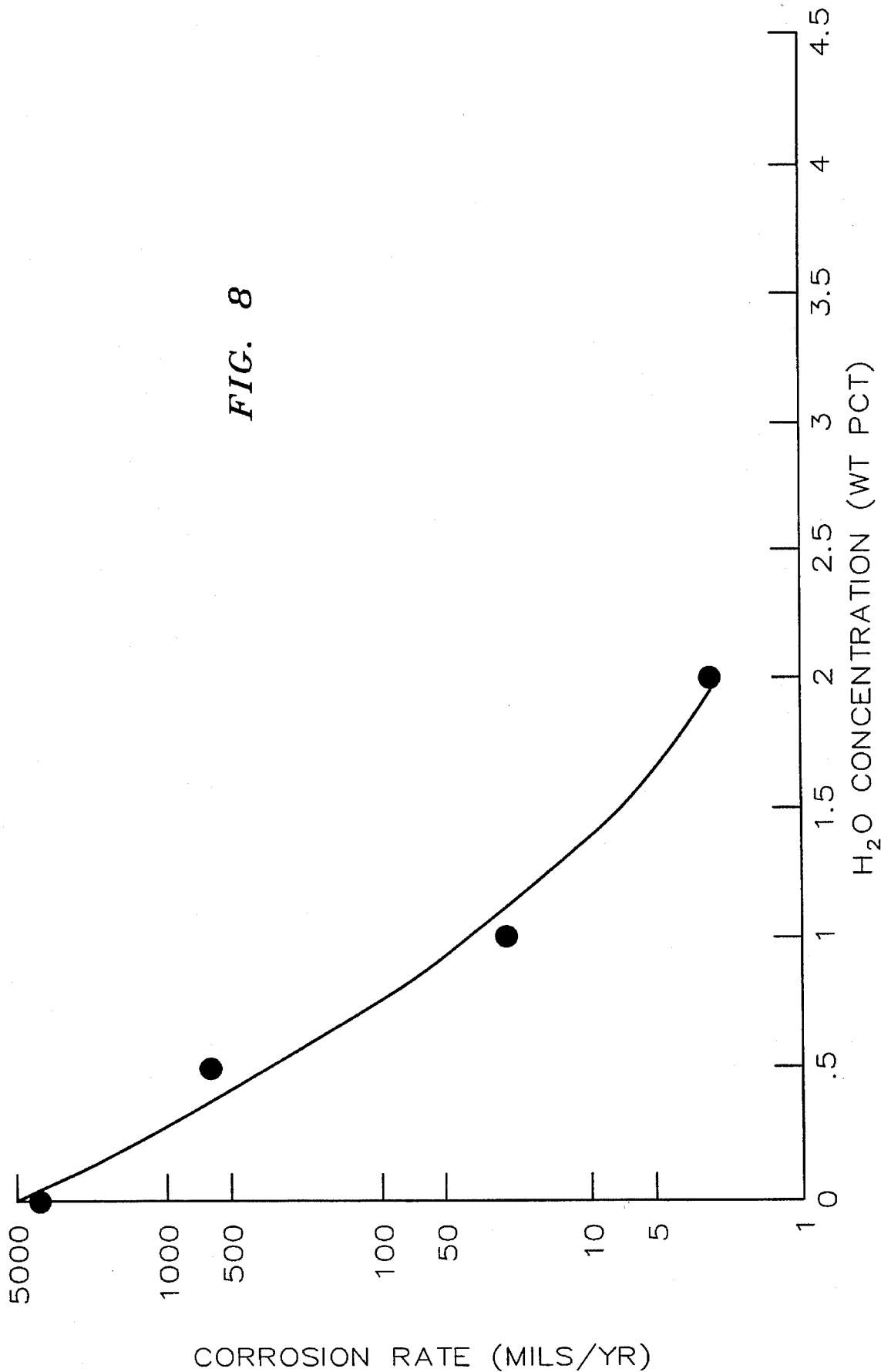
FIG. 8 shows the effect of added water on the corrosion rate (plotted on the y-axis) of carbon steel exposed to a solution of sulfolane in hydrofluoric acid as a function of the water content (plotted on the x-axis) of the HF/sulfolane solution.

Results from Examples XXII–XXV are shown in Table D. A graph of corrosion rate as a function of water content is shown in FIG. 8.

TABLE D

Carbon Steel Corrosion Data

| Experiment # | Wt % $H_2O$ in Catalyst @ t = o | Corrosion Rate mils/yr | Comments |
| --- | --- | --- | --- |
| XXII | .005 | >4000 | Severe |
| XXIII | .5 | 636 | Severe, nonuniform |
| XXIV | 1.0 | 25 | Mild, uniform |
| XXV | 2.0 | 3 | Low, uniform |

The decrease in corrosion rate with the addition of a controlled amount of water is surprising and unexpected because it is well known in the refining industry that anhydrous HF can be contained in carbon steel, but that wet HF aggressively corrodes carbon steel and must be contained in a nickel-enriched corrosion resistant alloy such as Monel 400 brand alloy.

While this invention has been described in terms of the presently preferred embodiment, reasonable variations and modifications are possible by those skilled in the art. Such variations and modifications are within the scope of the described invention and the appended claims.

That which is claimed:

1. A method of inhibiting corrosion in an alkylation process which utilizes a catalyst system containing a hydrogen halide and a sulfone compound, comprising the step of:

incorporating into said catalyst system water in an amount sufficient to inhibit corrosion.

2. A method as recited in claim 1 wherein the weight ratio of said hydrogen halide to said sulfone compound is in the range of from about 1:1 to about 40:1.

3. A method as recited in claim 2 wherein said hydrogen halide is hydrogen fluoride.

4. A method as recited in claim 3 wherein said sulfone compound is sulfolane.

5. A method as recited in claim 4 wherein the amount of water incorporated into said catalyst system is in the range of from about 0.25 to about 10.0 weight percent based on the total weight of the hydrogen halide component and the sulfone compound.

6. A method as recited in claim 1 wherein the hydrogen halide of said catalyst system is hydrogen fluoride and said sulfone compound is sulfolane, and wherein the amount of water incorporated into said catalyst system is in an amount in the range of from about 0.5 to about 5.0 weight percent based on the total weight of said hydrogen halide and said sulfone compound and with the weight ratio of said hydrogen halide to said sulfone compound in said catalyst system being in the range of from about 2.3:1 to about 19:1.

7. A method as recited in claim 1 wherein the hydrogen halide of said catalyst system is hydrogen fluoride and said sulfone compound is sulfolane, and wherein the amount of water incorporated into said catalyst system is in an amount in the range of from about 0.25 to about 10.0 weight percent based on the total weight of said hydrogen halide and said sulfone compound and with the weight ratio of said hydrogen halide to said sulfone compound in said catalyst system being in the range of from about 1:1 to about 40:1.

8. A method as recited in claim 1 wherein the hydrogen halide of said catalyst system is hydrogen fluoride and said sulfone compound is sulfolane, and wherein the amount of water incorporated into said catalyst system is in an amount in the range of from about 0.5 to about 10.0 weight percent based on the total weight of said hydrogen halide and said sulfone compound and with the weight ratio of said hydrogen halide to said sulfone compound in said catalyst system being in the range of from about 2.3:1 to about 19:1.

9. A method as recited in claim 1 wherein the hydrogen halide of said catalyst system is hydrogen fluoride and said sulfone compound is sulfolane, and wherein the amount of water incorporated into said catalyst system is in an amount in the range of from 1.0 to 5.0 weight percent based on the total weight of said hydrogen halide and said sulfone compound and with the weight ratio of said hydrogen halide to said sulfone compound in said catalyst system being in the range of from 3:1 to 9:1.

10. A method for decreasing the rate of corrosive attack on carbon steel by a mixture of HF and sulfolane, said method comprising adding a controlled amount of water to said HF and sulfolane mixture such that the resulting HF/sulfolane/ water mixture contains from about 0.25 to about 10 weight percent water.

11. A method as recited in claim 10 wherein said mixture of HF and sulfolane contains a weight ratio of the HF to sulfolane in the range of from about 1:1 to about 40:1.

12. A method as recited in claim 10, wherein said mixture of HF and sulfolane contains a weight ratio of the HF to sulfolane in the range of from about 2.3:1 to about 19:1.

13. A method as recited in claim 10 wherein said mixture of HF and sulfolane contains a weight ratio of the HF to sulfolane in the range of from 3:1 to 9:1.

14. A method as recited in claim 11 wherein said resulting HF/sulfolane/water mixture contains from about 0.5 to about 10 weight-% water.

15. A method as recited in claim 12 wherein said resulting HF/sulfolane/water mixture contains from about 0.5 to about 10 weight-% water.

16. A method as recited in claim 13 wherein said resulting HF/sulfolane/water mixture contains from about 0.5 to about 10 weight-% water.

17. A method as recited in claim 14 wherein said resulting HF/sulfolane/water mixture contains from 1.0 to 5 weight-% water.

18. A method as recited in claim 15 wherein said resulting HF/sulfolane/water mixture contains from 1.0 to 5 weight-% water.

19. A method as recited in claim 16 wherein said resulting HF/sulfolane/water mixture contains from 1.0 to 5 weight-% water.

\* \* \* \* \*